United States Patent
Kychakoff et al.

(10) Patent No.: US 9,414,024 B2
(45) Date of Patent: Aug. 9, 2016

(54) TERAHERTZ IMAGING

(75) Inventors: George Kychakoff, Maple Valley, WA (US); Peter Ariessohn, Lake Tapps, WA (US)

(73) Assignee: ENERTECHNIX, INC., Maple Valley, WA (US)

( * ) Notice: Subject to any disclaimer, the term of this patent is extended or adjusted under 35 U.S.C. 154(b) by 531 days.

(21) Appl. No.: 13/261,636

(22) PCT Filed: Oct. 12, 2011

(86) PCT No.: PCT/US2011/001751
§ 371 (c)(1),
(2), (4) Date: Apr. 12, 2013

(87) PCT Pub. No.: WO2012/050612
PCT Pub. Date: Apr. 19, 2012

(65) Prior Publication Data
US 2013/0222571 A1      Aug. 29, 2013

Related U.S. Application Data

(60) Provisional application No. 61/404,988, filed on Oct. 12, 2010.

(51) Int. Cl.
| | | |
|---|---|---|
| *G01N 1/40* | (2006.01) | |
| *H04N 7/18* | (2006.01) | |
| *G01J 11/00* | (2006.01) | |
| *G01N 21/3581* | (2014.01) | |
| *G01N 21/85* | (2006.01) | |
| *G01N 21/15* | (2006.01) | |

(52) U.S. Cl.
CPC . *H04N 7/18* (2013.01); *G01J 11/00* (2013.01); *G01N 21/3581* (2013.01); *G01N 21/8507* (2013.01); *G01N 2021/151* (2013.01)

(58) Field of Classification Search
None
See application file for complete search history.

(56) References Cited

PUBLICATIONS

Bassi, Jason, et al. "Terahertz time-domain spectroscopy of high-pressure flames." Frontiers of Energy and Power Engineering in China 3.2 (2009): 123-133.*
Pashkin, Alexej. Terahertz spectroscopy of ferroelectrics and related materials. Diss. Ph. D. thesis, Charles University in Prague, Faculty of Mathematics and Physics, 2004.*
Schuster, Franz, et al. "Broadband terahertz imaging with highly sensitive silicon CMOS detectors." Optics Express 19.8 (2011): 7827-7832.*

* cited by examiner

*Primary Examiner* — Sath V Perungavoor
*Assistant Examiner* — Clifford Hilaire
(74) *Attorney, Agent, or Firm* — J. Michael Neary (57) ABSTRACT

An imaging system with the ability to produce clear images of deposits inside operating high temperature process equipment such as kraft recovery boilers and power utility boilers uses a terahertz/mm-wave imaging system. This system allows direct inspection capability and the ability to directly measure deposit thickness on tubes and other interior surfaces at all locations within the boiler and precipitator. Terahertz and mm-wave imaging systems employ active imaging in which a beam of terahertz or mm-wave radiation generated within the imaging system is used to illuminate a region of the scene under investigation. The reflected radiation is collected by a lens or mirror system and focused onto a detector that converts the collected radiation into an electrical signal. Both the illuminating beam and the receiving optics are scanned across the scene in a raster fashion to produce a time-varying signal that is converted into an image of the scene.

17 Claims, 8 Drawing Sheets

TERAHERTZ IMAGING

This is related to and claims priority for U.S. Provisional Application No. 61/404,988 filed on 12 Oct. 2010 entitled "Terahertz Imaging In Boilers" and to PCT Application No. PCT/US2011/001751 filed on 12 Oct. 2011, which was published as international publication No. WO 2012/050612 on 19 Apr. 2012 entitled "Terahertz Imaging In Boilers".

This invention pertains to imaging in high temperature process equipment such as Kraft recovery and power utility boilers and in cement kilns, and also to quantitative measurement of the thickness of deposits on boiler tubes and other interior surfaces in places where it has not been possible to see clearly before owing to obscuration by particle laden gases with strong molecular emission and absorption lines. Such particle-laden gases include gases resulting from the combustion of coal, black liquor, or any other "dirty" fuel and places include the interior of furnaces such as coal-fired boilers, oil-fired boilers, chemical recovery boilers and cement clinker coolers.

BACKGROUND OF THE INVENTION

Boilers are a key component of coal-fired power plants and all kraft pulp mills, being the production bottleneck in most such mills. For financial reasons, it is therefore critical to avoid unscheduled boiler outages and to maximize the run times of these boilers. In order to prevent forced outages due to plugging of the convective passages around boiler tubes, sootblowers are used to remove saltcake deposits from the boiler tubes, but as currently employed, sootblowers are often not very effective and the current use of sootblowing steam is inefficient. Sootblowers are often operated on a fixed schedule with little or no feedback based on the actual degree of fouling in any given region of the convective section. Currently the principal means for collecting direct information on the degree of fouling is through the use of infrared inspection cameras such as those currently marketed to the pulp and paper, cement, and power generation industries. While these systems provide relatively clear images of the front of the superheater and in the sootblower lanes in the generator section, their ability to provide images at the back of the generator bank, in the economizer, and in the precipitator) or to provide images of deposits in the gas passages between tube banks is severely limited. Imaging in the economizer is limited by the relatively low temperatures and correspondingly low levels of thermal radiation, low contrast in that part of the boiler, and by the limited sensitivity of current infrared imaging sensors.

The limitation on imaging in the gas passages is the result of the geometry of the boiler and the fact that deposits in these regions cannot be seen from the inspection ports located on the side walls of the boiler. It is possible, with a suitable periscopic lens system that can be inserted into the boiler, to obtain images of deposits in the gas passages between tube banks. However, this periscopic lens tube is extremely expensive and suffers from relatively poor optical quality. Therefore, there is a need for an imaging system that can produce clear images of deposit formation throughout the interior of the process equipment such as a boiler—even in areas of low temperature such as the economizer or precipitator. There is also a need for an imaging system capable of producing images in areas that are currently inaccessible due to geometric constraints imposed by the construction of the boiler.

Another key unmet need is to be able to quantitatively measure the thickness of deposits on boiler tubes and other internal surfaces of the process equipment to enable the operator to assess the degree of fouling of these interior surfaces, such as convective pass tubing. Deposits on such tubes impede heat transfer and, if left unchecked, can eventually block the gas passages between the tubes causing a forced outage which, as discussed above, can be extremely costly. A much better approach would be to quantitatively measure the thickness of deposits on boiler tubes. This capability would provide real-time information on deposit buildup and sootbiower effectiveness and would facilitate implementation of feedback-controlled sootblowing allowing substantial reductions in sootblowing steam usage.

SUMMARY OF THE INVENTION

Accordingly, this invention provides an imaging system with the ability to produce clear images of deposits inside operating high temperature process equipment such as kraft recovery boilers and utility boilers using a terahertz/mm-wave imaging system. Such a system allows direct inspection capability and the ability to directly measure deposit thickness on tubes and other interior surfaces at all locations within the boiler and precipitator.

The terahertz region of the electromagnetic spectrum is variously taken to extend from 0.1 THz (100 GHz) or 0.3 THz (300 GHz) to about 3 THz (at the upper end of the infrared portion of the spectrum) and is sometimes referred to as the far infrared. Millimeter-wave frequencies are commonly defined to cover the range from about 30 GHz to about 300 GHz but sometimes this range is taken to extend to as much as 2,000 GHz. Thus, there is a substantial overlap between what is referred to as THz and what is called millimeter-wave (mm-wave) radiation. In the rest of this disclosure, the region from 100 GHz to 3 THz will be referred to alternately as the THz/mm-wave region, the THz region or the mm-wave region interchangeably.

The operation of terahertz and mm-wave imaging systems is completely different from current infrared imaging systems. Modern infrared imagers generally rely on the emission of thermal radiation from the scene itself. A lens system collects and focuses this thermal radiation onto a passive detector array that converts the infrared radiation in each portion of the scene into electrical signals that can be displayed as a visible image. Terahertz and mm-wave imaging systems would instead employ an active imaging approach in which a beam of terahertz or mm-wave radiation generated within the imaging system is used to illuminate a region of the scene under investigation. The reflected radiation is collected by a lens or mirror system and focused onto a single element detector that converts the collected radiation into an electrical signal. Both the illuminating beam and the receiving optics are scanned across the scene in a raster fashion to produce a time-varying signal that can be converted into an image of the scene. Because these imaging approaches employ active illumination, they are not limited by the inherent brightness of the scene and can be used to image regions such as the economizer or precipitator which do not emit sufficient radiation to produce clear infrared images.

There are numerous techniques that could be used for producing terahertz radiation. One method would employ a femto-second laser to produce a pulse of visible or near infrared radiation. This light pulse would be focused onto a nonlinear crystal or photoconductive antenna which, through optical rectification, would convert the visible or near infrared radiation into a femto-second terahertz pulse. This terahertz pulse is then collimated and used to illuminate the scene. The reflected terahertz radiation is detected by a gated photoconductive antenna which produces an electrical output proportional to the electric field intensity of the terahertz radiation. The gating is produced by illuminating the receiving antenna with a portion of the femto-second laser pulse used to generate the terahertz illumination beam. By varying the delay between the generated terahertz pulse and the gating of the receiving antenna, a time domain signal can be produced representing the time dependent intensity of the reflected terahertz pulse. A Fourier transform of this signal yields the spectrum of the reflected terahertz energy which is indicative of the wavelength-dependent absorption of the deposits at the interrogation point, and of the intervening gas along the line of sight within the frequency range of the terahertz pulse. This method is considered suboptimal because the alignment and timing accuracy required to implement this method successfully would be difficult to achieve in a simple and reliable device in an industrial environment.

The visibility inside boilers, in the mid-infrared, various according to particle loading. It is relatively clear in kraft recovery boilers, but greatly degraded in coal-fired boilers burning lower grades such as lignite by scattering of the infrared radiation by suspended particulates in the gases. In utility power boilers and cement kilns, the suspended particulates in the gases are also much larger and produce a nearly opaque atmosphere, making imaging very difficult. Some of these particles have diameters on the same order as the wavelength of the infrared radiation which results in high scattering efficiency and poor visibility. The wavelengths of Terahertz and millimeter wave radiation, on the other hand, are much longer than that of infrared radiation (1 THz corresponds to a wavelength of 0.3 mm); therefore, in this frequency range (because the particles are much smaller than the wavelength of the probing radiation) scattering by particles is many orders of magnitudes weaker than in the infrared. Nevertheless, in the mm-wave/THz spectral region, the wavelength is still short enough to provide required image resolution. For these reasons, mm-wave/THz imaging provide significantly better visibility than infrared imaging inside boilers and other furnaces.

A very important additional capability offered by this type of imaging system is the ability to quantify the thickness and shape of deposits on boiler tubes in real time. THz imaging employs extremely short duration pulses of radiation to illuminate the scene, making it possible to measure the distance to the illuminated spot with high precision by measuring the time delay of the reflected pulse. Resolutions of a few picoseconds are thus possible which translates to sub-millimeter distance resolution. Measurement of the distance to each point within the scene provides a map of the surface position of the deposits throughout the scene which can be translated into a tube deposit map using a model of the boiler tube locations from construction drawings or from measurements performed after a water-wash when the tubes are clean. The thickness of the deposits can also be determined by measuring the time delay between the THz pulse reflected from the surface of deposits and the pulse reflected from the metal tube surface beneath the deposits. Millimeter wave radar systems accomplish the same thing by using very broad band continuous, wave illumination. By performing a Fourier transformation of the reflected data, time domain information that provides time resolution of about ten picoseconds can be obtained. This type of mm-wave radar system in a kraft recovery boiler is capable of producing clear images of boiler tubes at the back of the generating bank and of measuring the thickness of deposits on the tubes.

This invention provides an improved imaging system based on millimeter wave imaging technology to produce clear images of surface deposits throughout the convective sections of the process equipment, such as boilers, etc., including in regions where there is very little ambient illumination, such as at the bottom of the economizer. In addition, this system provides quantitative measurements of the thickness and size of the deposits allowing for accurate feedback on the degree of fouling on each surface, such as boiler tubes. By employing time-domain spectroscopy (TDS) to measure the chemical composition of the deposits, this invention enables on-line detection of corrosion-related chemistries—in real-time. This technology lends itself to the implementation of a robust, side-looking imaging system that can be incorporated into sootblowers to provide imaging capability in the gas passages between tube banks which otherwise cannot be viewed from existing sidewall inspection ports due to geometrical constraints of the boiler geometry. This would allow for complete, continuous monitoring throughout the convective sections of the boiler. Such a system could be used not only to provide information on tube deposits, but also to detect excessive tube deflection and to allow inspection of the generator tube attachments at the steam drums—a common point of failure.

There is also a great need for these capabilities in kraft recovery boilers, in coal-fired boilers, in biomass boilers, and in spray drying applications such as skim milk dryers (where deposits on the dryer surfaces can present an ignition hazard).

The rapid development of new technology for generating and detecting mm-wave radiation—driven by the current interest within the security and military communities—offers a very bright future for the application of this technology in the process industries and promises to provide increasingly effective, robust, and economical components which can be used in products that address the needs of these industries.

The use of the invention to reduce sootblowing steam usage without increasing the rate of boiler tube fouling has substantial benefits in terms of energy, economics and the impact on the environment. As an example, recovery boilers usually operate two-to-four sootblowers at all times, each one consuming approximately 20,000 lbs of steam per hour. Assuming that, on average, boiler operates 24/7 for 350 days per year, the sootblowing steam usage amounts to about $5.04 \times 10^8$ pounds per year per boiler, or approximately $8.57 \times 10^{10}$ pounds per year for the 170 recovery boilers in operation in the US.

The most common current practice is to operate sootblowers on a timed schedule developed from past experience of boiler plugging behavior. Sootblowers are operated in all areas at least some of the time just to be safe, but there is currently no means to determine and localize the instantaneous state of boiler tube fouling throughout the convective sections in order to determine where deposits are forming or to assess the effectiveness of individual sootblowers in removing deposits. This invention will enable direct observation and measurement of deposits on the tubes and allow sootblowers to be operated only when and where they are needed. Because a complete feedback-control system for adjusting the operation of sootblowers in real-time has never been implemented in a kraft recovery boiler, no operational data exists on the potential benefits that could be realized through the implementation of such a system; there is no precise data to show the amount of sootblowing steam that can be saved by not blowing in areas where there are no deposits and concentrating on areas where fouling is occurring. Prior attempts to reduce sootblowing steam usage have not employed any feedback mechanism (other than visual inspection at the end of a run) to dictate where and when to reduce sootblowing. Direct observation with infrared imaging systems in operating kraft recovery boilers has shown that sootblowers often are operated in areas where boiler tubes are relatively clean and deposit buildup is proceeding slowly. Sootblowing could easily be reduced in these areas with little negative impact on overall boiler cleanliness. Therefore, a conservative estimate would be that, at a minimum, a 10% reduction in sootblowing steam usage can be achieved without increasing boiler plugging by employing the proposed technology.

Whether the additional steam made available by reduced sootblowing is used to offset purchased power or to offset other sources of steam in the pulp mill, it will be possible to reduce the amount of coal, fuel oil, or natural gas used by the electric utility or the fuel oil being burned in other boilers in the pulp mill to produce the same process steam. In either case, the emissions from the combustion of those fuels would be eliminated.

Approximately half of the electricity in the US is generated from the combustion of coal. According to a 1995 Environmental Protection Agency publication, the standard (AP42) for calculating emission factors for coal combustion dictates levels of 1.75 lb of $SO_x$/MMBTU, 1.19 lb of NOx/MMBTU, and 240 lb of $CO_2$/MMBTU. If the postulated 10% reduction in sootblowing steam frees up electricity derived from coal combustion, this would translate into reductions of 8,177 tons/year of $SO_x$, 5,560 tons/year of $NO_x$, and 1.12 MM tons/year of $CO_2$ nationwide.

Fuel oil has a typical heat content of about 19,000 BTU/lb, so the anticipated reduction in sootblowing steam usage would make it possible to forego burning approximately 500 MM lb of fuel oil per year nation-wide. Combustion of fuel oil with a typical carbon content of 89% by weight produces approximately 3.263 lb of $CO_2$ per pound of fuel oil. Therefore, the reduction in $CO_2$ released to the atmosphere is expected to be on the order of 1.6 billion pounds (0.8 MM tons) per year nation-wide.

A recent EPA report indicates that typical emissions from boilers burning No. 6 fuel oil are ~2 lb of $SO_2$ and ~0.4 lb of NOx per MM BTU. For the anticipated reduction in oil usage, this translates into a reduction in $SO_2$ emissions of about 19 million lb/yr (9,345 tons/yr) and a reduction in NO emissions of 3.74 million lb/yr (1,869 tons/yr) nation-wide.

The benefits outlined above have been calculated solely on the basis of reduced sootblowing steam usage, but additional benefits may accrue from avoiding unplanned outages by detecting problems early enough to schedule an outage at a convenient time or take corrective action during a planned outage, and from avoiding damage to equipment by detecting and correcting problems before they lead to catastrophic failures. These benefits may actually dwarf the dollar value of the savings from sootblowing steam reduction—especially if they involve avoiding long periods of lost production. A recent presentation at the St. Petersburg Recovery Cycle meeting put the cost of unscheduled downtime at between $100,000 and $300,000 per day. Avoiding even one unscheduled outage due to the ability to better monitor internal processes in the boiler could pay for the deposit monitoring system of this invention.

Two models have been developed to predict the transparency of the combustion environment inside an operating kraft recovery boiler at mm-wave and terahertz frequencies: 1) a Mie scattering model that predicts the extinction of light due to scattering and absorption by particles suspended in the combustion product gases, and 2) a molecular absorption model that predicts the absorption of radiation due to vibrational and rotational transitions of the combustion gas molecules.

Even in cases where the particles are nonabsorbing, light scattered by particles is randomized and loses its ability to convey image information. Therefore, the parameter that is of importance in predicting the impact of particles on visibility is the extinction coefficient which is the sum of the scattering and absorption coefficients.

In order to predict the extinction of light due to scattering it is necessary to specify the size distribution and concentration of particles in the recovery boiler environment. The particles present inside the boiler derive from a variety of combustion-related processes that take place inside the boiler. Among these are in-flight drying, pyrolysis, and burnout of black liquor droplets to form char (carryover) particles; ejecta and fragments from these char particles are believed to be the source of intermediate size particles. Vaporization of sodium or sodium compounds from the smelt bed or from burning liquor droplets and char particles and the reaction of these sodium species with $SO_2$ and $CO_2$ form sodium sulfate and sodium carbonate fume particles. It has long been accepted within the recovery boiler community that fume particles are present in high concentrations and that the mean size of these particles is in the range of 200 to 500 nm. The particulates in a utility power boiler are primarily ash, minerals and other particles from the burning of coal powder in the boiler burner.

Figure 1:
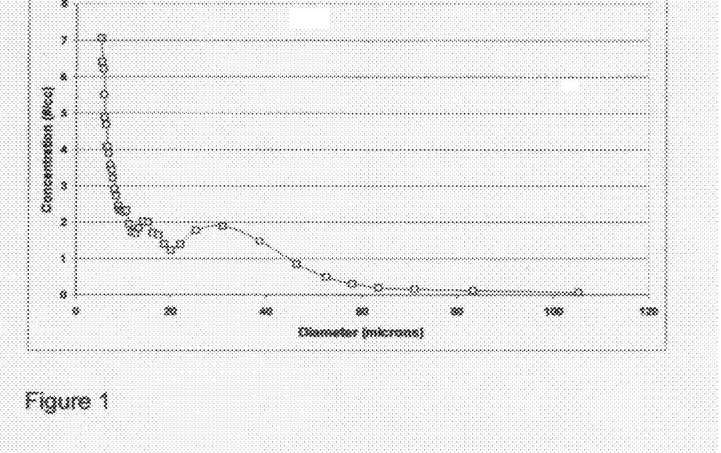
FIG. 1 is a graph showing size distribution of intermediate size particles in a recovery boiler.

In the late 1990's, Dr. Ariessohn and Dr. Donald Holve performed laser light scattering measurements inside two different recovery boilers. They established the presence of significant numbers of intermediate-size particles (ISPs) with diameters in the 5 to 100 micron diameter range, which are believed to be formed by fracturing of char particles during in-flight combustion and also by ejection of material as the organics in the liquor droplet vaporize explosively during volatilization. Virtually no carryover particles of a size greater than 100 micron diameter were observed in the upper furnace. The size distribution measured in this study is shown in FIG. 1

From these data, one can calculate the extinction of light due to these two size classes of particles (fume and ISPs) separately and add their contributions to obtain an overall estimate of light extinction due to particle scattering. A Mie scattering model has been constructed which calculates the extinction coefficient as a function of size parameter ($=\pi D/\lambda$) assuming spherical particles. For each particle diameter and radiation wavelength, the extinction coefficient can then be determined from a look-up table. These extinction coefficients are then weighted by the concentrations of particles of that particular diameter. The contributions from all size classes are then summed to obtain the overall extinction coefficient for a particular wavelength of radiation due to the size distribution of particles under consideration.

While the extinction due to fume is dominant in the visible and near infrared part of the spectrum, the extinction due to fume in the mm-wave and THz regions of the spectrum is several orders of magnitude smaller than that due to ISPs because of the much larger ratio of wavelength to particle size in that spectral region. The maximum extinction coefficient for ISPs (at a wavelength of 10 microns) is only about 0.037 $m^{-4}$ and decreases rapidly with increasing wavelength.

Experience with infrared imaging in recovery boilers has shown that attenuation of as much as 20% still allows for reasonably clear images. Therefore, we can safely conclude that extinction by suspended particles will have little or no effect on visibility in the mm-wave and THz spectral range. Furthermore, it is quite apparent that attenuation due to particle scattering and absorption will be much smaller in the mm-wave region (frequencies below 0.3 THz) than at higher frequencies.

Using the molecular absorption modemodel, predictions of molecular absorption have been generated using the HITRAN spectroscopic database of molecular parameters. This database contains parameters for more than 2.7 million molecular transitions. These parameters can be used to calculate the intensity and width of absorption features resulting from mixtures of 39 molecular species. Harvard University maintains the HITRAN database and makes it available to researchers; they also provide a software program (JAVA-HAWKS) which facilitates translating the molecular parameters into spectroscopic parameters specific to particular species or mixtures and particular gas temperatures. We have created models based on these data that permit the calculation of molecular absorption spectra for arbitrary mixtures of gases over specified path lengths at a number of temperatures.

This model allows the user to specify an arbitrary molecular gas composition, the total spectral range to cover, and the spectral resolution (bandwidth) to use in generating the spectrum. The gas mixture shown above is typical of the combustion gases inside a kraft recovery boiler. The three dominant species are nitrogen, water vapor and carbon dioxide.

Figure 2:
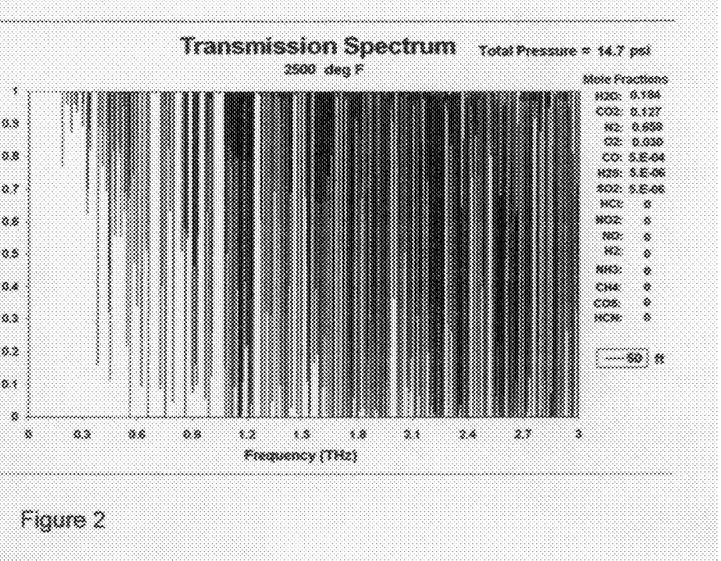
FIG. 2 is a plot showing the THz/mm-wave transmission spectrum of recovery boiler gases

A sample spectrum is shown in FIG. 2. This figure shows that there are numerous strong absorption features at frequencies greater than 1 THz. However, there are windows where the transmission is predicted to be near 100% over a 50 foot path in the region of 1.05, 0.96, 0.83 and 0.71 THz. At frequencies less than 0.4 THz (400 GHz), this gas mixture is seen to be relatively transparent with only a few isolated, relatively weak absorption features.

Figure 3:
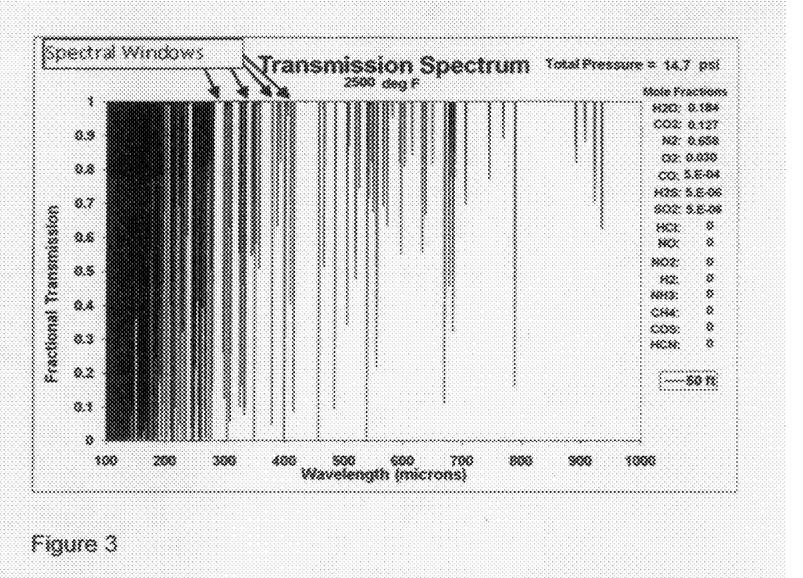
FIG. 3 is a plot of the THz/mm-wave spectrum of recovery boiler gases

This same spectrum is shown in FIG. 3, plotted against wavelength; this gas mixture is highly transparent at wavelengths longer than about 700 microns. Spectra were also generated for temperatures of 2000, 1500, 1000 and 500 degrees F., which showed only very slight differences in the absorption spectra as a function of temperature.

Figure 4:
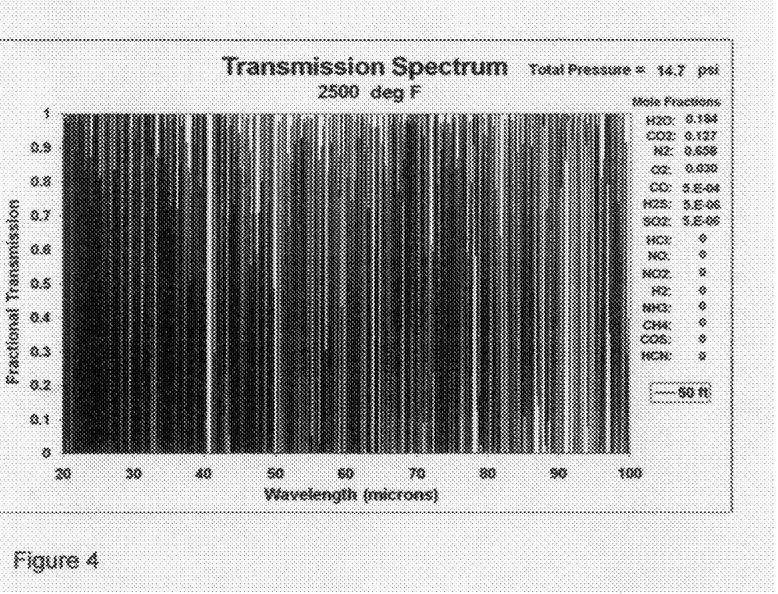
FIG. 4 is a plot of the long-wave infrared spectrum of recovery boiler gases

The model has also been run for wavelengths between 20 and 100 microns and shows that there are virtually no spectral windows in that region due to numerous water vapor absorption bands (see FIG. 4).

Figure 5:
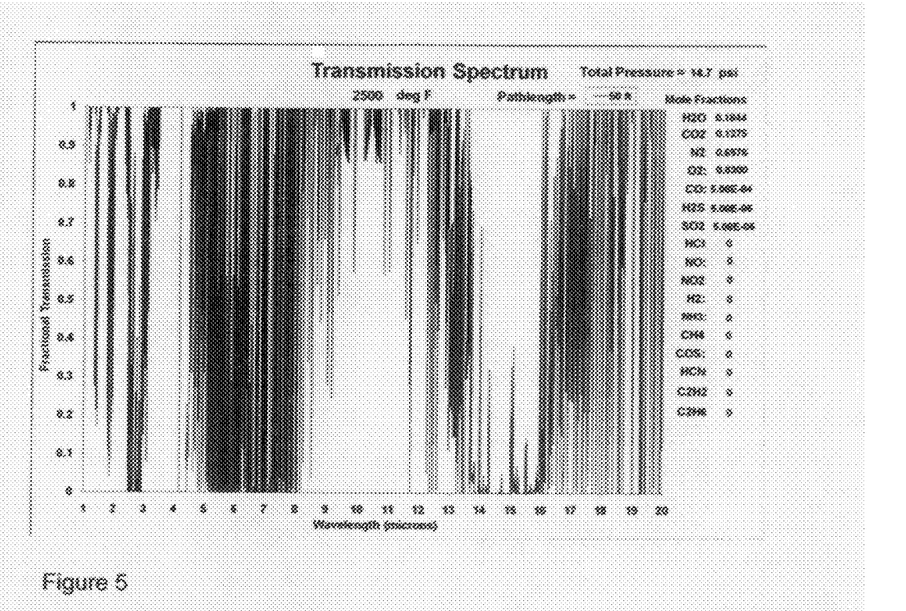
FIG. 5 is a plot of the near- and mid-infrared spectrum of recovery boiler gases

In the near and mid-infrared (1 to 20 microns), absorption by many of the species present in the recovery boiler atmosphere are significant and offer only a few narrow spectral windows. The 8 to 12 micron "atmospheric" window that is quite clear in the earth's atmosphere is less clear in the combustion atmosphere due to the presence of $CO_2$ hot bands (see FIG. 5).

From this study, it is clear that the combustion product gases inside a recovery boiler are much clearer in the mm-wave region than they are in the near-, mid-, or long-wave infrared and that there are several transparent windows in the THz region that are comparable in transparency to the windows in the near- to mid-infrared. The frequency of operation for best results is selected from among the following specific transparent "windows" in which imaging and measurement may best be performed: 499.0 to 503.5 GHz, 505.5 to 524.0 GHz, 525.0 to 530.0 GHz, 532 to 540 GHz, 542 to 546 GHz, 550 to 554 GHz, 558 to 571 GHz, 573 to 578 GHz, 580 to 594 GHz, 596 to 620 GHz, 622 to 645 GHz, 647 to 658 GHz, 659 to 724 GHz, 726 to 734 GHz, 736 to 751 GHz, 754 to 766 GHz, 768 to 775 GHz, 777 to 793 GHz, 795 to 840 GHz, 843 to 853 GHz, 855 to 863 GHz, 866 to 898 GHz, 908 to 916 GHz, 918 to 922 GHz, 928 to 967 GHz, 972 to 978 GHz, 980 to 987 GHz, 989 to 1.000 THz, 1.006 to 1.068 THz, 1.070 to 1.077 THz, 1.088 to 1.095 THz, 1.100 to 1.108 THz, 1.122 to 1.130 THz, 1.230 to 1.271 THz, 1.299 to 1.322 THz, 1.444 to 1.472 THz, 1.476 to 1.493 THz, 1.497 to 1.516 THz, 1.545 to 1.563 THz.

Thus, the two models developed to study attenuation of electromagnetic radiation due to particle scattering and absorption, and due to molecular absorption by combustion product gas species have confirmed that the recovery boiler atmosphere would be much more transparent at mm-wave and THz frequencies than in the near and mid infrared.

DESCRIPTION OF THE DRAWINGS

The invention and its attendant features and benefits will become better understood upon reading the following description of the preferred embodiments in conjunction with the following drawings, wherein.

DESCRIPTION OF THE PREFERRED EMBODIMENTS

A portable, THz measurement system for performing tests in an industrial plant environment starts with microwave frequency radiation and uses non-linear mixers to up-convert the radiation to higher frequencies. The equipment required for this latter process is much more robust and less expensive than femto-second laser equipment, but can produce radiation in roughly the same frequency band. A field hardened system operating at frequencies of 95 to 225 GHz (0.095 to 0.225 THz) has been built and tested, and another system that will operate at up to 0.3 or possibly 0.5 THz has been designed.

Both 100 and 200 GHz systems use an Agilent vector network analyzer (VNWA). The microwave frequency (12.5-

Figure 6:
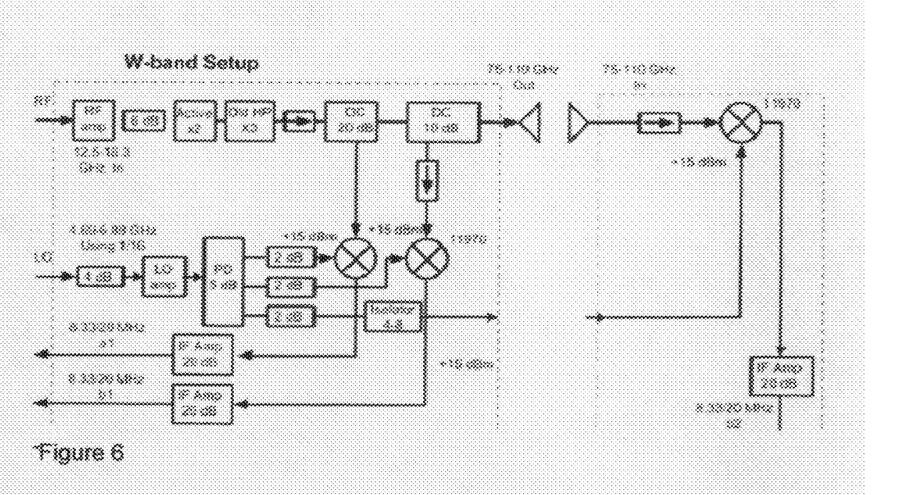
FIG. 6 is a block diagram of W-band (75-110 GHz) frontend.

18.3 GHz) is multiplied by 6 to create 75-110 GHz and by 12 to create 140-220 GHz. The received mm-wave signal is down-converted into an intermediate frequency in the radar frontend (FIG. 6) and processed by the VNWA. The radar front-ends are portable and can be mounted on a tripod to scan the region of interest; all the measurements are conducted in the broadband frequency-domain. Time-domain information is obtained by taking the Fourier transform of the band-limited frequency-domain signal; the time resolution is approximately given by $\delta t=1$/bandwidth. The tripod is equipped with a stepping motor controlled rotational stage. Our scanning mm-wave radars, therefore, can obtain 2-D images which consist of the down-range (distance) using the time-domain data and cross-range using the angle scan. Addition of a vertical scan capability allows us to generate 3-D images. The current system has separate transmitting and receiving antennas with collimating lenses. With this system, the 3-dB antenna beam width is approximately 0.5 deg at 100 and 200 GHz.

To test the performance of the system, we performed laboratory measurements of two 76-mm diameter metal pipes with and without ~7 mm thick plastic covers. The pipes were mounted vertically 6" apart at a distance of about 15 feet from the mm-wave radar apparatus. The time delay between the reflection from the front of the plastic covering and the reflection from the pipe was about 65 picoseconds, which corresponds to a the round trip distance through the plastic and back again, and was close to the actual thickness (plus a small air gap). This demonstrates the ability to accurately measure the thickness of a "deposit" on a metal tube in the laboratory using the time difference between the multiple reflections to determine the spatial separation between the partially reflecting surfaces.

Although a better down-range (time) resolution can be obtained with a wider bandwidth, a broadband mm-wave system is also much more expensive; therefore, it would be desirable to identify the optimum combination of center frequency and bandwidth to produce a system with adequate spatial and temporal resolution to produce clear images of the boiler tubes and to measure deposit thickness accurately at reasonable cost. Better horizontal (and vertical) spatial resolution can be obtained by increasing the frequency and increasing the antenna diameter, however, the size of typical inspection ports limits the size of the antenna that can be used unless the value of the system can justify installing larger openings.

We have experimentally demonstrated improved visibility relative to IR imaging in a combustion environment using THz/mm-wave radiation, showing not only that THz waves can propagate through the recovery boiler environment with minimal attenuation, but also experimentally demonstrating the ability to use THz/mm-wave radiation to produce clear images of boiler tubes in an area of the boiler where infrared imaging can, at best, produce images of marginal quality, and demonstrating the ability to distinguish reflections from the surface of boiler tubes and from the surface of saltcake deposits on the outside of the boiler tubes. The time delay between these reflections can readily be measured and this information can be used to make real-time, quantitative measurements of saltcake deposit thickness—a capability that has never before been demonstrated.

There are three factors which can compromise visibility of infrared imaging in recovery boilers: 1) Interference from Molecular Absorption and Emission, and from Scattering and Absorption by Suspended Particles.

In the infrared—within the 3.9 micron spectral window—atmospheric interference due to molecular absorption is minimal over path lengths typically encountered in a recovery boiler, however extinction due to particle scattering and absorption can have a significant effect on visibility.

2) Lack of Contrast in the Scene

In some regions of the boiler, objects within the scene may offer little contrast. This is especially true if all surfaces are coated with deposits at nearly the same temperature. In this case, the radiation emitted or reflected from all surfaces is of nearly the same intensity and it becomes difficult to discern any detail. This phenomenon is commonly observed in ceramic kilns. When the objects being fired reach the temperature of the kiln, they become virtually invisible.

3) Insufficient Illumination

The third obstacle to good visibility is the lack of sufficient illumination or emission to produce a useful image. In this case, the intensity of the light delivered to the imaging system is insufficient to produce a signal substantially greater than the noise level of the imaging device which, again, results in very low contrast.

The water inside the boiler tubes as it enters the generating bank is close to saturation at the pressure of the steam being produced by the boiler. Typically this means the tube temperature at that point is 490-600 deg F. The temperature of the gas exiting the generating bank is typically between 600 and 700 deg F., so surfaces coated with saltcake will have surface temperatures only slightly higher than the bare tubes. Therefore, if all surfaces have a uniform coating of saltcake, they may be at very nearly the same temperatures and there may be only slight differences in brightness.

A portable mm-wave imaging system was tested in a kraft recovery boiler. The system was transported to the mill and set up at the back of the boiler where there was a 2 foot square opening with a hinged metal door. The economizer section had been removed from this boiler, so there was a clear view of the back of the generator bank from this location.

A heat shield transparent to mm-waves, consisting of an alumina/silica mixture was used to cover the boiler opening. In this configuration, separate transmitter and receiver lenses and transducers were used. In future systems, a single transmitter/receiver unit may be employed to reduce the size and complexity of the system.

The mm-wave imaging system was scanned in the horizontal plane to produce a 2-dimensional (angle and time) image of the boiler tubes. Measurements were made at several different frequencies and using a range of bandwidths.

Field Experiments in Recovery Boilers

Field measurements were conducted using both 94 GHz and 200 GHz systems at a kraft pulp mill. Mm-wave radar reflection data were obtained prior to and following a water wash which allowed us to obtain images of fouled and clean boiler tubes from the same measurement location; the radar data obtained in the post-washing period provided images of bare pipes.

Figure 7:
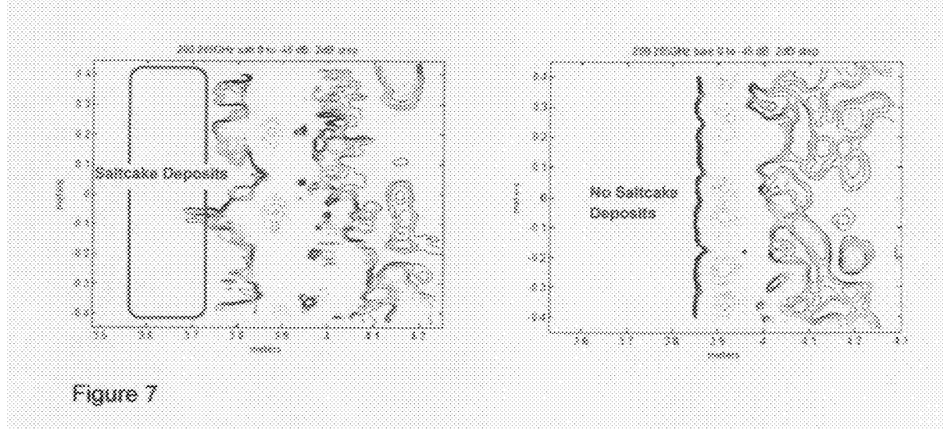
FIG. 7 are two contour plots of metal pipes in rectangular coordinates after distance correction and level adjustment using radar frequency of 200-205 GHz; tubes with deposits on the left; clean tubes following the water wash on the right.

FIG. 7 shows contour plots of the same scene in the horizontal plane (x-y axis in units of meters). The presence of saltcake is clearly visible. On the left, the deposits on the tubes are seen as protrusions towards the left (towards the mm-wave radar system), whereas on the right, the front surface of the tubes (the back of the generator bank) is seen to be free of those protrusions. In these figures, the transformation from time to distance was made without taking into account the refractive index of the saltcake. Therefore, the thickness of the deposit shown may be overestimated by a factor of between 1.4 and 1.85. Applying this correction the measured deposit thickness are consistent with visual observation of the tubes made after the boiler was shut down, but before they did the water wash.

The time-domain data with saltcake clearly shows pulse broadening due to reflections from air-saltcake and saltcake-metal interfaces. The time-domain results for the case with a bandwidth of 20 GHz can clearly separate the air-saltcake interface from that of saltcake-pipe. In other words, this system can accurately estimate the thickness of the saltcake deposit. These results also show the importance of identifying optimum frequency and bandwidth for this application.

We have demonstrated that, even in an area of the boiler where infrared imaging produces a marginal image, the mm-wave radar system can obtain clear reflection images of boiler tubes. We have also demonstrated that the mm-wave system can distinguish reflections from the tubes and from the overlying deposits and can provide quantitative data that can be used to infer deposit thickness.

Fixed Location System

The experimental prototype that was tested in the recovery boiler is already fairly close to what is required for an industrial sensor. Improvements incorporated into a commercial sensor replace the 2 antenna/lens system with one that employs a single antenna/lens. By developing a system that operates at higher frequency, the size of the antenna/lens can be reduced. This system does not require a large opening since the transmitter/receiver head is only 2 to 3 inches in diameter and the scanning mirror can be placed very close to the port opening. This system can therefore function using a port that involves only a single tube bend, greatly improving cost-effective access to the process. A special port covering that prevents hot gases from escaping from the boiler and damaging the equipment is employed.

Figure 8:
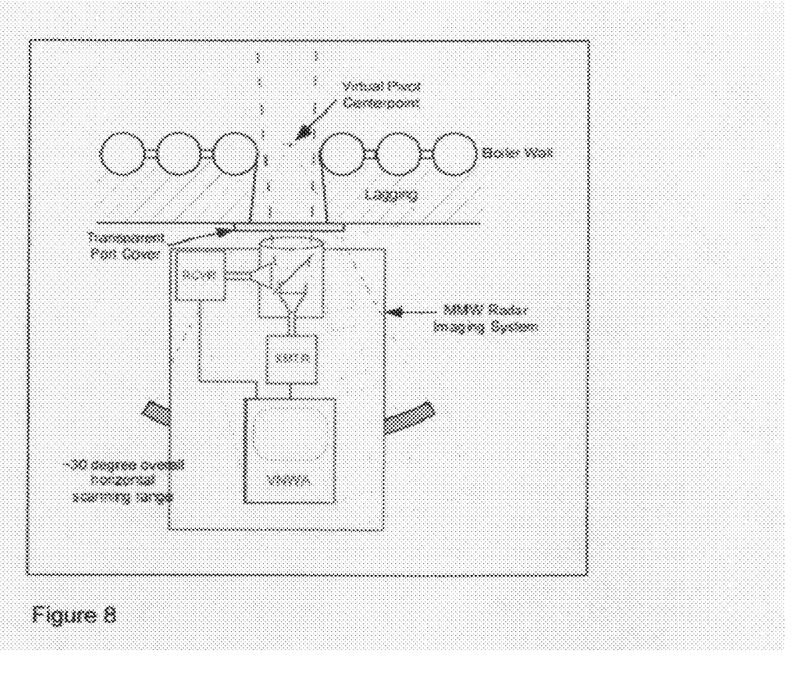
FIG. 8 is a schematic plan view of an arrangement for fixed mount scanning MMW radar deposit monitor.

A scanning system for propagating the transmitted and received electromagnetic radiation through a small inspection port in the side of a large enclosure containing the high temperature combustion environment is shown in FIG. 8. A virtual pivot can be used conveniently to provide scanning motion with a center of rotation flush with the inside surface of the boiler wall. This allows for scanning over a very wide field of view, while allowing all the components to be located behind the port covering, as shown schematically in FIG. 8. Enertechnix manufactures virtual pivot systems for use with infrared imaging technology and their adaptation for use with the mm-wave imaging system is straight-forward (see FIG. 8). Nevertheless, in some situations it may be necessary to employ a port that is wider than the standard inspection port in order to achieve wide angle coverage of the interior of the boiler. For the mm-wave imaging system, it may be necessary to include an encoder to measure the angular position. In addition, to maximize the deposit area probed by the system, it may be necessary to include vertical scanning.

Figure 10:
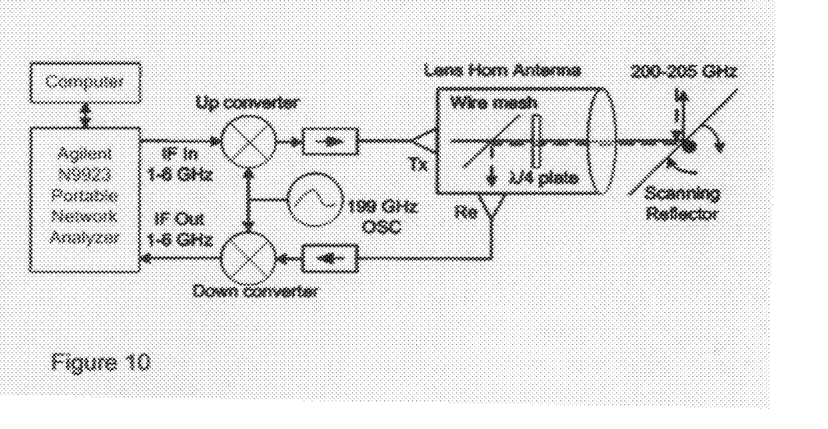
FIG. 10 is a block diagram of 200 GHz imaging radar

An alternative approach would be to utilize a scanning mirror as shown in FIG. 10. This would allow for rapid scanning in both the horizontal and vertical directions with fine resolution.

Sootblower-Mounted System

Figure 9:
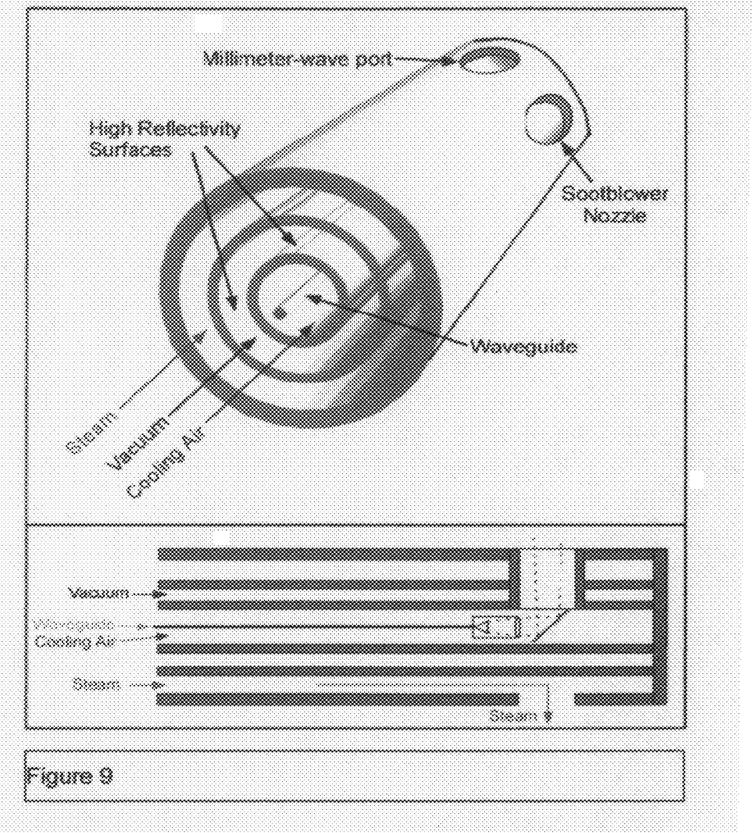
FIG. 9 is a sootblower providing thermal protection of integrated mm-wave imager.

We have performed a thermal analysis of a special sootblower tube that can be used to provide a platform for an imaging/measurement system for propagating the transmitted and received electromagnetic radiation through a small inspection port in the side of a large enclosure containing the high temperature combustion environment device allowing it to be inserted into the furnace to perform inspections of regions that are not visible from ports on the outer walls of the boiler. This design is shown schematically in FIG. 9; a triple wall pipe is used to provide a passage for steam flow and, at the same time, to provide adequate thermal insulation for the imaging system components. Steam flowing in the outermost annular passage ensures that the temperature at the outer surface of the middle annular passage is well below the furnace gas temperature. The middle annular passage is evacuated and has highly reflective inner surfaces (nickel or chrome plated, as in a Thermos bottle) to minimize heat transfer. In this case, the bore of the structure would carry the mm-wave components and also cooling air. Thermal modeling of this structure has shown that it will be possible to continuously maintain the mm-wave components below 100 F with only about 12 cfm of cooling air flow. In the design shown in FIG. 9, the mm-wave components inside the sootblower probe consist of a metal waveguide, a horn antenna (also metal), a lens that can be made of Teflon or high resistivity silicon, and a mirror. None of these components should be particularly sensitive to temperature and can certainly survive at temperatures well above 100 deg F. (Teflon can operate continuously above 400 deg F.). The cooling air flowing out through the mm-wave port in the side of the probe will prevent infiltration of saltcake particulate and combustion product gases. In this design, the sootblower provides both axial and rotational motion, eliminating the need for a scanning mirror.

We have investigated the availability of commercial components that could be used to construct a fixed location THz/mm-wave imaging system suitable for continuous use in an operating recovery boiler. FIG. 10 is a schematic diagram of these components together with a portable, low-cost network analyzer that can be incorporated into such a system; the network analyzer generates a 1-6 GHz signal that is up-converted to ~200 GHz by mixing it with a reference signal from a 199 GHz local oscillator. A horn antenna (labeled Tx in the figure) produces a mm-wave beam that passes through a wire mesh beam splitter and a quarter wave plate that converts the beam from linear to circular polarization. This beam passes through a Teflon lens that narrows the spread of the beam, allowing it to be projected over long distances. The beam is reflected from the surface of a scanning mirror that directs the beam towards the scene to be imaged and allows it to be scanned in both the horizontal and vertical directions in a raster pattern. The reflected radiation is collected and focused by the Teflon lens and directed through the same quarter wave plate which converts the circularly polarized radiation back to linear polarization with an orientation perpendicular to that of the transmitted beam. This allows the received beam to be reflected by the wire mesh beam-splitter and prevents crosstalk between the transmitted and received beams. The received beam is collected by a second horn antenna (labeled Re in the figure) which couples the radiation into a waveguide. This signal is down converted back to a 1 to 6 GHz signal by mixing it with the 199 GHz reference signal. The resulting signal is detected by the network analyzer. A computer is used to Fourier transform the output of the network analyzer from the frequency domain to the time domain allowing for precise measurements of the time delay between reflections from the tubes and from the surfaces of the deposits on the tubes. The computer is also used to control the scanning mirror and provide a user interface.

A radar system operating at 300 GHz compared with that at 200 GHz radar offers some desirable benefits. Different front-end configurations and a single antenna system which uses circular polarization to separate the reflected and incident beams also provide attractive benefits. Mm-wave up- and down-convertors allow us to use a regular VNWA with limited bandwidth, and a single converter to perform both up-conversion and down-conversion by suitable time gating offers yet additional commercial advantages.

Low-cost, ruggedized mm-wave/THz imaging and measurements in kraft recovery and power boilers offer the ability to obtain 3-dimensional boiler tube images and quantitative deposit thickness measurements in an operating recovery and power boiler and it makes possible to incorporate that functionality in an integrated, miniaturized, and ruggedized mm-wave sensor.

The dielectric constants of deposits in different environmental conditions are important parameters for estimating the thickness of saltcake deposits. The mm-wave image results from reflections at the two surfaces of the saltcake deposit (the gas/saltcake interface and the saltcake/boiler tube interface) and from absorption of the mm-wave radiation within the saltcake deposit. The reflection coefficients at these two interfaces depend on the optical properties of the saltcake and the time delay between these reflections is determined by the propagation time of the mm-wave radiation in the saltcake deposit which depends on the deposit thickness and on the dielectric constant of the saltcake. The dielectric constant of many crystalline materials depends on temperature due to thermal expansion—increased temperature results in decreased density and a decrease in dielectric constant. However, saltcake deposits in a recovery boiler are subject to a much more complex, irreversible sintering process that depends on temperature, time and composition. At temperatures as low as ~500 C (932 F), low melting point eutectics may form due to the presence of impurities (primarily chlorides and potassium) and the deposits will undergo an irreversible consolidation. Over time, voids will disappear and the deposit will become much denser. It is best to take into account the impact of this process on dielectric constant to obtain the most accurate and consistent deposit thickness measurements.

Figure 11:
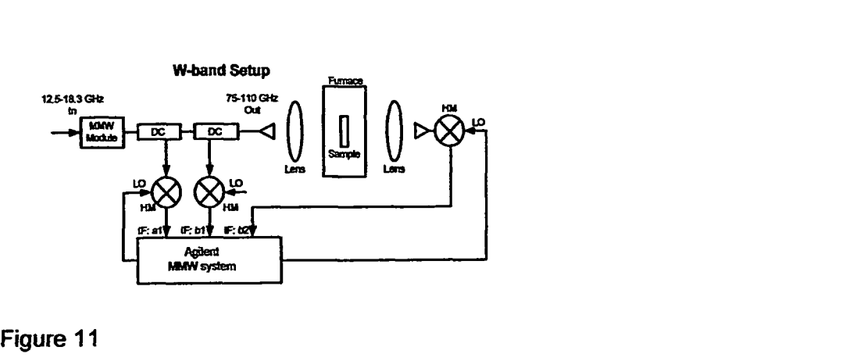
FIG. 11 is a schematic of a dielectric constant measurement at high temperature setup (up to 1200 C)

For refractive index measurements, saltcake is crushed into a powder and packed into a void created between two Styrofoam sheets to create a planar structure. It is important to note that the crushed saltcake sample has relatively low density due to voids and may be similar to some actual deposits in the cooler regions of the boiler where sintering doesn't occur, but these samples were clearly not representative of sintered saltcake deposits that would be found in the superheater or, possibly, in the front of the generator bank. The apparatus required to make these measurements is shown in FIG. 11. We conduct detailed saltcake characterizations from 75-325 GHz and at temperatures up to about 90° C. using this system. The experimental setup for 140-220 GHz and 220-300 GHz is similar.

The results of this study allow us to determine the accuracy with which we can estimate deposit thickness from mm-wave radar measurements and also enable us to assess the feasibility of making measurements at higher frequencies where the absorption properties of the saltcake may preclude such measurements. Obtaining spectral absorption data from the saltcake that can be correlated with its composition provides the capability to identify the presence of species that are associated with accelerated corrosion.

Figure 12:
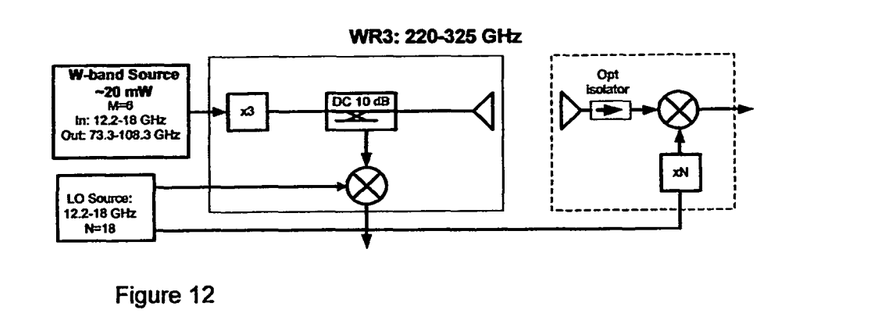
FIG. 12 is a simplified block diagram of the 300 GHz radar frontend.

A new radar front-end operating at 300 GHz operates with the basic principle as with the 100 and 200 GHz front-ends, and the same VNWA can be used as the processing unit. A simplified diagram is shown in FIG. 12. This modular design is suited for both reflection (radar) and transmission (material characterization) measurements. It includes several WR3 (220-325 GHz) items including a multiplier, directional coupler, and harmonic mixer. A W-band source with a Spacek amplifier as the RF source complete the 300 GHz frontend and a sub-harmonic mixer are used to improve the signal-noise-ratio. Either 3" or 2" lens horn antennas will be used for collimating the beam. Two lens horn antennas, sub-harmonic mixer, W-band source, LO amplifier, and isolators are used.

Figure 13:
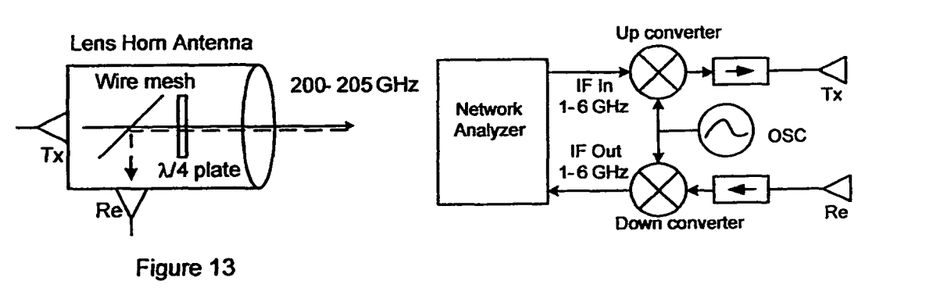
FIG. 13 is a schematic of a single antenna system on the left, and a schematic of up- and down-convertors configuration on the right.

A dual antenna radar has many advantages including minimum coupling between transmitter and receiver channels. However, alignment can be simplified and the size of the system can be reduced by using a single antenna for both transmitting and receiving. This is particularly important for measurements made through a small inspection port. The antenna configuration of a single antenna system is shown in FIG. 13. To separate the received signal from the transmitted one, the transmitted signal is circularly polarized (eg. LHC). Since the reflected radiation usually has the opposite polarization (RHC), a $\lambda/4$ plate and wire mesh beam-splitter can be used for converting the polarization and separating the transmitted and received signals. Circularly polarized radar is less sensitive to scattering by small particles. This is an important advantage for a mm-wave radar system operating in a kraft recovery boiler.

A 200 GHz single antenna system can be constructed with a $\lambda/4$ wave-plate and wire mesh beam-splitter. The up- and down conversion section incorporates several low-cost VNWAs operating at up to 6 GHz. If the thickness of the saltcake deposits can be estimated accurately using a 5 GHz bandwidth at 200 GHz in combination with models and a-priori data (discussed below), it is possible to use a low cost VNWA for processing the data.

An alumina/silica material works effectively as a heat shield for providing protection from furnace gases and particles, and has sufficient structural rigidity and strength to act as a suitable seal over an open port boiler while being transparent to the millimeter wave frequencies. However, this material is somewhat soft and fragile and may offer only a short working life for continuous operation in a recovery boiler environment. The alumina/silica material is also available in the form of ceramic tiles. A material such as Transite™ which is used to line chimney flues would serve well as a heat shield material in this application due to its strength and refractory properties, depending on its transparency to THz/mm-wave radiation. Ceramics and other composite materials are also possibilities.

It is preferable to prevent saltcake from building up on the inside of the heat shield. Mechanical rodding or scraping, high velocity air jets, steam cleaning, periodic rapping, or a combination of these methods can be used to prevent excessive saltcake buildup on the heat shield.

It appears that a bandwidth of 20 GHz is sufficient to resolve deposit thicknesses of 2 mm. However, a saltcake layer of more than 10 mm may create significant attenuation and the reflection from the metal cylinder may not be detectable. The saltcake appears to be quite a bit more transparent at 100 GHz than at 200 GHz. Therefore, it may be possible to switch frequency to produce accurate measurements of saltcake deposits of various thicknesses (higher frequencies for thin layers and lower frequencies as the deposit thickness increase).

Clear images of the interior of a recovery boiler and saltcake deposits measurements on tubes can be obtained using THz/mm-wave radiation. The images obtained with that system provided 2-dimensional data (horizontal scan angle plus distance measurements). In addition, with an enhanced THz/mm-wave imaging system it is possible to obtain 3-dimensional images of the interior of the recovery boiler (horizontal and vertical scan angles plus distance). The selection of center frequency and bandwidth provides high fidelity data for both the tubes and the deposits and allows the system to clearly distinguish reflections from the front surfaces of the deposits and reflections from the boiler or wall tubes. This data can be used to quantify the thickness of the deposits and obtain autonomous operation of the sensor at a fixed location (illumination of the target, collection of the reflected radiation, analysis of the data, and reporting of the results). The system can also have the ability to self-calibrate, eliminating the need for a calibration surface outside the boiler.

A low-cost, integrated mm-wave deposit imaging radar system can be built around the recently introduced Agilent N9923 portable microwave network analyzer (NWA) shown in FIG. 10. The front-end employs a single lens horn antenna which uses circular polarization and a wire mesh polarizing beamsplitter to separate the received signal from the transmitted signal as above. The beam scan can be performed either by using a rotating reflector as shown in FIG. 10, a virtual pivot mount similar to that shown in FIG. 8, or a rotational stage. The up- and down-conversion of the 1-6 GHz IF signal from the VNWA uses two mixers and a 199 GHz LO (local oscillator) source. A receiver based on a low-cost FMCW for intermediate frequency signals can also be used, but, since typical FMCW radars have a bandwidth of less than 1 GHz, this approach may not be suited for the detection of a thin saltcake layer.

The invention can be useful in many applications in which high temperatures or dirty atmospheres (or both) hinder data collection. For example, steel making has long needed a system for collection of data regarding the conditions inside furnaces. Information regarding the level of the steel bath and thickness of the slag layer are useful for proper positioning of oxygen lances and electric arc electrodes inside the furnaces to achieve the most efficient and efficacious operation, and knowledge of the thickness and chemical composition of the slag layer on top of the molten steel bath enables the operators to adjust the operating parameters and chemical additions to achieve with improved accuracy the desired composition of the steel and minimize tap-to-tap times for maximum throughput of the furnace.

Figure 14:
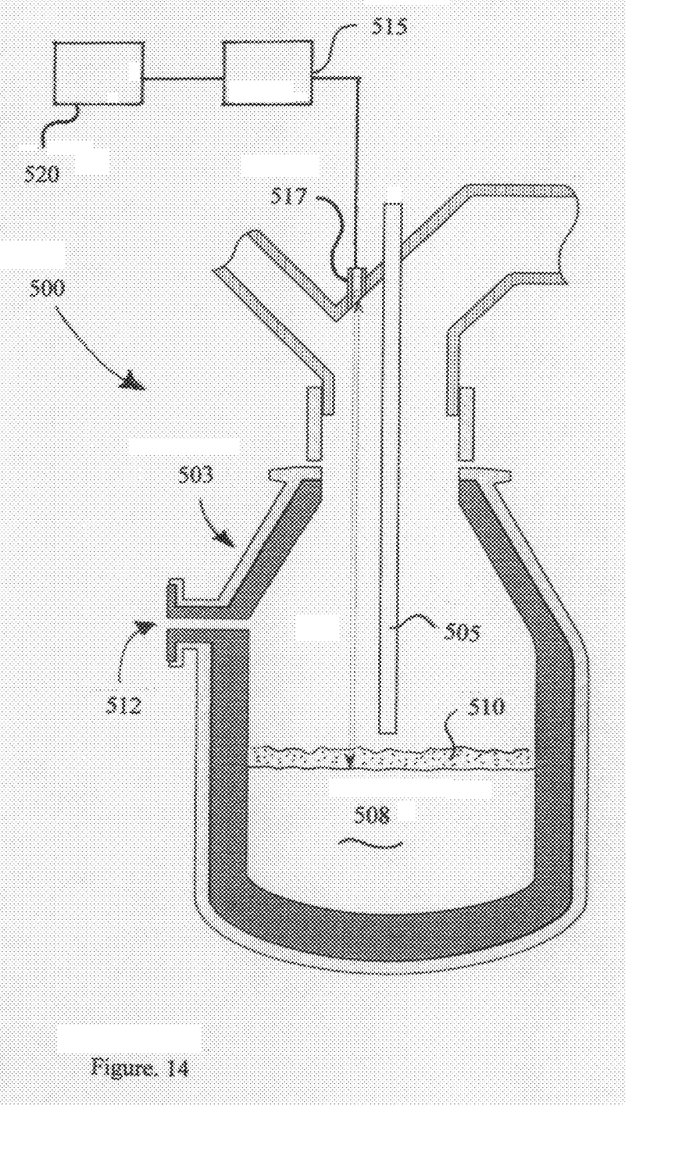
FIG. 14 is a schematic elevation of a steel making basic oxygen furnace incorporating a terahertz imaging system in accordance with the invention, the electronics of which are shown in block diagram form.

As shown in FIG. 14, a basic oxygen furnace 500 has a refractory-lined converter 503 into which molten metal is charged, usually from a blast furnace (not shown). Additional materials are added and an oxygen lance 505 is lowered to inject a supersonic stream of oxygen into the bath of molten metal, raising its temperature and increasing the thickness of the slag layer 510. When the processing is complete, the converter 503 is tipped to discharge the molten steel through a tap 512 for subsequent operations.

An electronics unit 515 is coupled to a horn antenna 517 for transmitting a terahertz/mm wave signal into the surface of the slag layer 510 and the molten metal bath 508. The electronics unit 515, shown in more detail in FIG. 16, converts the reflected signal into useful information which is displayed in the factory control room on a display unit 520.

Figure 15:
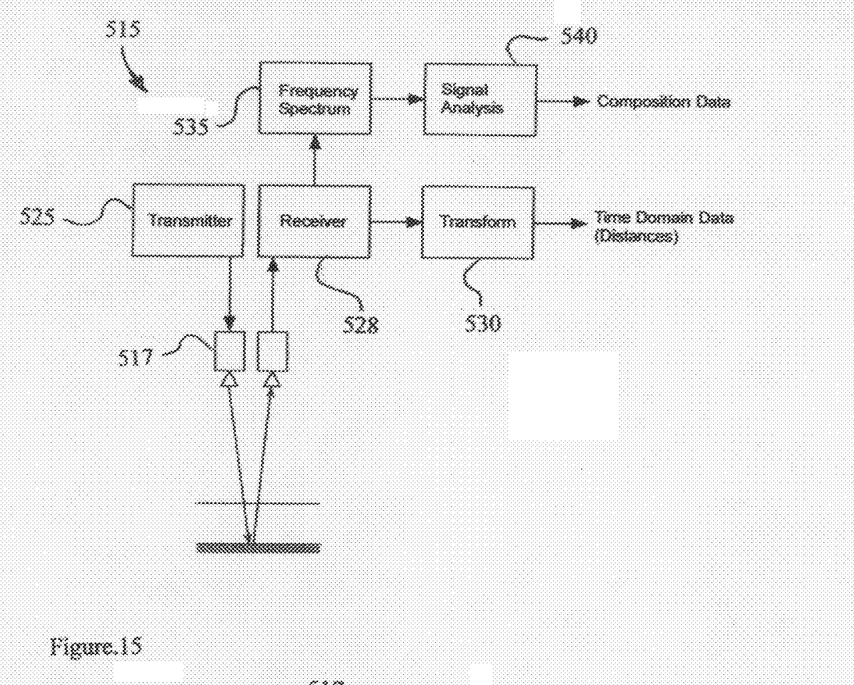
FIG. 15 is a block diagram of the imaging electronics used in the furnaces of FIGS. 14 and 16.

A transmitter 525 in the electronics unit 515 generates a stepped series of fixed frequency tones. These are closely spaced in frequency and cover a wide range of frequencies. The larger the frequency range, the finer the time resolution (and the finer the distance resolution). The signals reflect off of the slag layer 510 and the molten metal bath surface 508 and are detected by a receiver 528, which sends the output from the receiver to a transform unit 530, which in turn performs a Fourier Transform or a chirp Z transform or some other known transform that converts the amplitude and phase information from the frequency data into time data from which distance can be calculated based on the known (or assumed) speed of light in each medium. In the gas it's essentially the same as the speed of light in a vacuum. In the slag, it will depend on the composition and density of the slag. This tells the operators what the level of the molten metal bath is and also the thickness of the slag layer 510.

Frequency data from the receiver 528 is also sent to a frequency spectrum block 535 which converts the amplitude and phase at each frequency of the stepped frequency signal into real and imaginary components of the complex permittivity at each frequency. Since the permittivity of the gas is pretty much the same as that of a vacuum, this signal will provide information primarily on the properties of the slag. We can also subtract the signal due to the reflection off the upper surface of the slag from the signal reflected from the steel to get only the part representing the propagation through the slag. A signal analysis block 540 will take the data on the complex permittivity of the slag as a function of frequency and convert it into composition information. Since the permittivity of the various components may not have distinct features (such as narrow absorption peaks) in the frequency range covered by the measurement, the curves for some of the components may not differ very much from one another. In that case, the signal analysis block 540 would include a form of chemometric analysis (partial least squares, principal component analysis, etc.). These methods are extremely good at recognizing very subtle differences in spectra resulting from the presence of components with very similar spectra and are widely used in chemical analysis.

Figure 16:
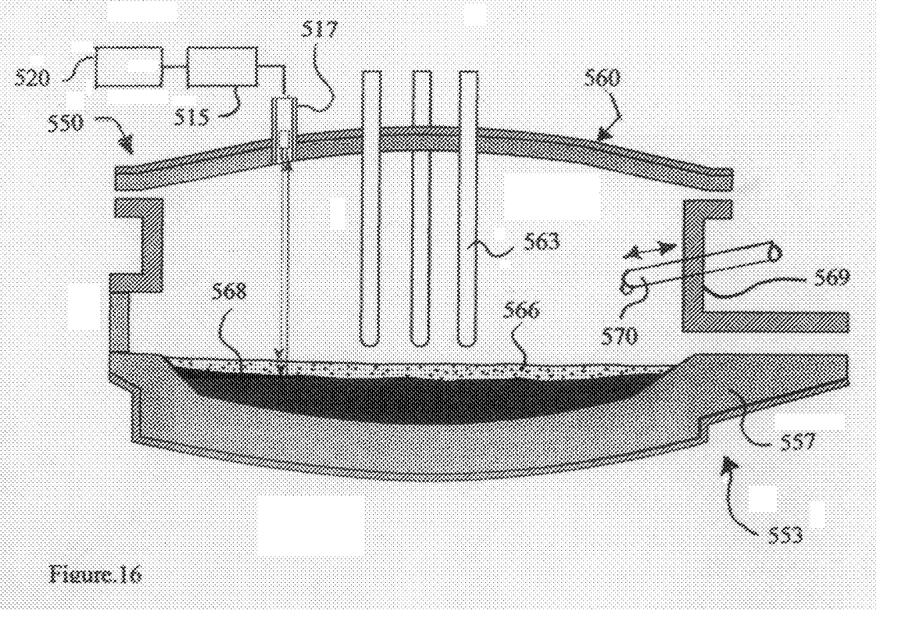
FIG. 16 is a schematic elevation of an electric arc furnace incorporating a terahertz imaging system in accordance with the invention, the electronics of which are shown in block diagram form.

An electric arc furnace shown schematically in FIG. 16 includes a converter 553 lined with refractory 557. A lid 560 has electrodes 563 mounted on supporting structure (not shown) for feeding electrical power to the electrodes and moving them vertically through openings in the lid 560. The power is at high voltage and when it is exposed in the atmosphere above the contents in the converter 553 produces intense radiation that can damage the refractory. Thus, it is good practice to keep the arc buried in the scrap to be melted in the converter or immersed in the slag layer 566 above the molten metal bath 568 after the metal scrap has been melted enough to create a molten metal bath. Several burners (not shown) are mounted in the side walls 569 are used to help melt the scrap metal in "cold" zones between the electrodes 563, and an axially movable oxygen lance 570 is mounted on a supporting structure for injecting oxygen into the molten metal bath. The position of the oxygen lance relative to the surface of the molten metal bath is important to know to ensure it is at the optimal position for stirring the molten metal bath and producing the desired chemical and heating effects in the bath.

A horn antenna 517 is connected to an electronics unit 515 and through it to a display unit 520 in the factory control room, as in the basic oxygen furnace shown in FIG. 14. The description of the function of those elements is the same and is not repeated here.

Obviously, numerous modifications and variations of the described preferred embodiment are possible and will occur to those skilled in the art in light of this disclosure of the invention. Accordingly, we intend that these modifications and variations, and the equivalents thereof, be included within the spirit and scope of the invention as defined in the following claims, wherein we claim:

The invention claimed is:

1. A terahertz/mm-wave imaging system for producing images and quantitative measurements of internal geometric structures, such as steam tubes and interior walls, inside high temperature industrial process units that are visually inaccessible by infrared imaging owing to obscuration by particle laden gases with strong molecular emission and absorption lines, such as power utility boilers, kraft recovery boilers, cement kilns and petrochemical refinery furnaces, comprising:

a generator for generating an illuminating beam of wave radiation in terahertz/mm electromagnetic spectrum, limited to frequencies of operation within the terahertz /mm wave range at which there is minimal obscuration by suspended particles or molecules in the gas, to illuminate said internal structures within said high temperature industrial process units; a receiver, having a field of view, for collecting a portion of the illuminating beam radiation after reflection from the internal structures inside said units; and electronics/software for converting said collected radiation into an electrical signal, and for interpreting said electrical signal to yield information about said geometric structures, such as the presence and thickness of surface deposits on such structures, wherein said frequencies of operation are selected within the range of 100 GHz to 3 THz but avoids specific frequencies where the gases exhibit strong absorption features;

said specific frequencies where the gases exhibit strong absorption features include the strongest such absorption features below 500 GHz at 183.5 GHz, 232.7 GHz, 293.8 GHz, 321.4 GHz, 325.3 GHz, 331.2 GHz, 336.5 GHz, 380.6 GHz, 390.6 GHz, 403.3 GHz, 426.1 GHz, 437.7 to 448.4 GHz, 463.4 GHz, 471.3 GHz, 475.1 GHz, and 488.6 GHz.

2. A terahertz/mm-wave imaging system as defined in claim 1, further comprising:
a system for scanning said illuminating beam and said receiver's field of view across selected interior portions of said units, and said electronics/software converts electrical signals from said generator and receiver into an image or map of said scene.

3. A terahertz/mm-wave imaging system as defined in claim 2, wherein:
said images reveal formation and growth of deposits on heat transfer surfaces; which at wavelengths shorter than the terahertz/mm band are obscured by particle laden gases, including gases resulting from the combustion of coal, black liquor, biomass, or any other "dirty" fuel in the interior of furnaces such as coal-fired boilers, oil-fired boilers, chemical recovery boilers and cement clinker coolers.

4. A terahertz/mm-wave imaging system as defined in claim 2, wherein said images are interpreted to give quantitative measurements of deposit thickness based on the time difference in the arrival of reflected energy from gas-deposit interface and from deposit-metal interface.

5. The imaging system of claim 4 in which the time difference between reflections from outer deposit surfaces and underlying metal surfaces are transformed into deposit thickness based on the propagation speed of the electromagnetic radiation in the deposit where this propagation speed is given by the speed of light in a vacuum divided by the real part of the refractive index of the deposit.

6. A terahertz/mm-wave imaging system as defined in claim 1, wherein:
said illuminating beam consists of a series of brief pulses of radiation with durations of less than 1 nanosecond, and amplitude and time of arrival of reflected pulses sensed by the receiver are measured;
said electronics/software uses said amplitude to indicate character of reflecting surfaces of said internal geometric structures, and uses said time of arrival of said reflected signal to indicate how far said reflecting surfaces are from said scanning system, whereby multiple reflections separated in time at a single position of the scanning system are indicative of multiple, partially reflecting surfaces located along a line-of-sight, such that time differences between said multiple reflections may be used to determine spatial separation between said partially reflecting surfaces.

7. A terahertz/mm-wave imaging system as defined in claim 1, wherein:
said illuminating beam includes a series of continuous, fixed frequency "tones" with a duration of many periods of oscillation of the particular frequency of each "tone", and in which a large number of such "tones" are transmitted in sequence and received at each position of the scanning system, the received phase and amplitude of the sequence of tones constituting a sampled frequency spectrum of the reflected energy which is then transformed using a transformation method, such as Fourier transformation, or Chirped-Z transformation, to produce a time-domain record representing the reflection/scattering from said internal geometric structures.

8. A terahertz/mm-wave imaging/measurement system as described in claim 1 wherein:
said frequencies of operation are selected from among the following specific transparent "windows" in which imaging and measurement may be performed 499.0 to 503.5 GHz, 505.5 to 524.0 GHz, 525.0 to 530.0 GHz, 532 to 540 GHz, 542 to 546 GHz, 550 to 554 GHz, 558 to 571 GHz, 573 to 578 GHz, 580 to 594 GHz, 596 to 620 GHz, 622 to 645 GHz, 647 to 658 GHz, 659 to 724 GHz, 726 to 734 GHz, 736 to 751 GHz, 754 to 766 GHz, 768 to 775 GHz, 777 to 793 GHz, 795 to 840 GHz, 843 to 853 GHz, 855 to 863 GHz, 866 to 898 GHz, 908 to 916 GHz, 918 to 922 GHz, 928 to 967 GHz, 972 to 978 GHz, 980 to 987 GHz, 989 GHz to 1.000 THz, 1.006 to 1.068 THz, 1.070 to 1.077 THz, 1.088 to 1.095 THz, 1.100 to 1.108 THz, 1.122 to 1.130 THz, 1.230 to 1.271 THz, 1.299 to 1.322 THz, 1.444 to 1.472 THz, 1.476 to 1.493 THz, 1.497 to 1.516 THz, 1.545 to 1.563 THz.

9. A terahertz/mm-wave imaging system as defined in claim 1, further comprising:
a scanning system for propagating the transmitted and received electromagnetic radiation through a small inspection port in a side of a large enclosure containing the high temperature combustion environment;
said scanning system employs a virtual pivot point located at the center of the port.

10. A terahertz/mm-wave imaging system as defined in claim 1, further comprising:
an imaging/measurement system for propagating the transmitted and received electromagnetic radiation through a small inspection port in a side of a large enclosure containing the high temperature combustion environment;
said imaging/measurement system components are placed inside a specially modified sootblower with a side-looking aperture through which the transmitted and received electromagnetic radiation can pass.

11. A terahertz/mm-wave system for producing quantitative information about physical dimensions of materials and structures that are visually inaccessible by infrared imaging owing to obscuration by particle laden gases with strong molecular emission and absorption lines inside high temperature industrial process units containing high temperature gasses such as power utility boilers, kraft recovery boilers, cement kilns, petrochemical refinery furnaces, and ore smelting or steel production, comprising:
a generator for generating an illuminating beam of electromagnetic radiation in a specific terahertz/mm-wave frequency range limited to frequencies of operation within the terahertz/mm wave range at which there is minimal obscuration by suspended particles or molecules in the gas, to illuminate, via an antenna, said internal materials and structures within said high temperature industrial process units;

a receiver for collecting a portion of the illuminating beam radiation after reflection from a reflective substrate on which said internal materials inside said units resides; and electronics/software for converting said collected radiation into an electrical signal, and for interpreting said electrical signal to yield physical dimension information about said internal materials and structures;

said generator is configured to emit said illuminating beam of electromagnetic radiation in a form including a stepped series of fixed frequency "tones" with a duration of many periods of oscillation of a particular frequency of each "tone" and in which a large number of such "tones" are transmitted and received in time-spaced transmitted periods and received periods;

wherein each of said received sequence of tones constitute a sampled frequency spectrum of the reflected energy having a phase and amplitude;

a transform unit in said electronics/software for transforming said sampled frequency spectrum of the reflected energy using as suitable transformation method such as Fourier transformation, Chirped-Z transformation to produce a time-domain record representing the reflection/scattering from said internal materials;

a frequency spectrum unit for converting the amplitude and phase at each frequency of said stepped series of fixed frequency "tones" into real and imaginary components of complex permittivity of said internal materials at each frequency, and producing signals carry data indicative of said complex permittivity; and a signal analysis unit for receiving said complex permittivity data and converting said data into composition information of said internal materials;

wherein said frequencies of operation are selected within the range of 100 GHz to 3 THz but avoids specific frequencies where the gases exhibit strong absorption features;

said specific frequencies where the gases exhibit strong absorption features include the strongest such absorption features found below 500 GHz at 183.5 GHz, 232.7 GHz, 293.8 GHz, 321.4 GHz, 325.3 GHz, 331.2 GHz, 336.5 GHz, 380.6 GHz, 390. 6 GHz, 403.3 GHz, 426.1 GHz, 437.7 to 448.4 GHz, 463.4 GHz, 471.3 GHz, 475.1 GHz, and 488.6 GHz.

12. A terahertz/mm-wave system as defined in claim 11 where said specific frequency range of the transmitted radiation is selected to lie within relatively transparent "windows" in the transmission spectrum of the gases inside said high temperature process units.

13. A terahertz/mm-wave system as in claim 11 where the specific frequency range of the transmitted radiation are in frequencies in the range of 100 GHz to 3 THz.

14. A method for producing quantitative information about internal materials that are visually inaccessible by infrared imaging owing to obscuration by particle laden gases with strong molecular emission and absorption lines, inside high temperature industrial process units, such as power utility boilers, kraft recovery boilers, cement kilns, petrochemical refinery furnaces, and ore smelting or steel production, comprising:

generating an illuminating beam of wave radiation in terahertz/mm electromagnetic spectrum limited to frequencies of operation within the terahertz/mm wave range at which there is minimal obscuration by suspended particles or molecules in the gas, said illuminating beam of wave radiation includes a stepped series of fixed frequency "tones" with a duration of many periods of oscillation of a particular frequency of each "tone" and in which a large number of such "tones" at different frequencies are transmitted and received in time-spaced transmitted periods and received periods;

illuminating said internal materials with said illuminating beam;

collecting a portion of said illuminating beam after reflection from a reflective surface on which said materials reside, whereby said illuminating beam passes through said internal materials inside said units twice, wherein each of said received sequence of tones constitute a sampled frequency spectrum of the reflected energy having a phase and amplitude;

converting said collected radiation into an electrical signal;

interpreting said electrical signal to yield information about said internal materials, said interpreting step includes:

a) transforming said sampled frequency spectrum of the reflected energy using as suitable transformation method such as Fourier transformation, Chirped-Z transformation to produce a time-domain record representing the reflection/scattering from said internal materials, and converting said amplitude and phase information from the frequency data into time data, and calculating distance based on the known (or assumed) speed of light in each medium to produce data distance of said materials from a reference point and the thickness of selected materials in said process units; and b) converting said amplitude and phase at each frequency of said stepped series of fixed frequency "tones" into real and imaginary components of complex permittivity of said internal materials at each frequency, and producing signals carry data indicative of said complex permittivity, and converting said data into composition information of said internal materials;

wherein said frequencies of operation are selected within the range of 100 GHz to 3 THz but avoids specific frequencies where the gases exhibit strong absorption features;

said specific frequencies where the gases exhibit strong absorption features include the strongest such absorption features below 500 GHz at 183.5 GHz, 232.7 GHz, 293.8 GHz, 321.4 GHz, 325.3 GHz, 331.2 GHz, 336.5 GHz, 380.6 GHz, 390.6 GHz, 403.3 GHz, 426.1 GHz, 437.7 to 448.4 GHz, 463.4 GHz, 471.3 GHz, 475.1 GHz, and 488.6 GHz.

15. A method as defined in claim 14 said frequencies lie in the range of 100 GHz to 3 THz.

16. A method for producing quantitative information about internal materials visually inaccessible by infrared imaging owing to obscuration by particle laden gases inside industrial process units containing high temperature gasses with strong molecular emission and absorption lines, comprising:

generating an illuminating beam of wave radiation in a specific terahertz/mm electromagnetic spectrum limited to frequencies of operation within the terahertz/mm wave range at which there is minimal obscuration by suspended particles or molecules in the gas, said illuminating beam of wave radiation including a stepped series of fixed frequency "tones" with a duration of many periods of oscillation of a particular frequency of each "tone" and in which a large number of such "tones" are transmitted and received in time-spaced transmitted periods and received periods;

illuminating said internal materials with said illuminating beam;

collecting a portion of said illuminating beam after reflection from a reflective surface on which said internal materials reside inside said units, whereby said beam passes through said materials twice, wherein each of said received sequence of tones constitute a sampled frequency spectrum of the reflected energy having a phase and amplitude;

converting said collected radiation into an electrical signal;

interpreting said electrical signal to yield information about said internal materials, said interpreting step includes transforming said sampled frequency spectrum of the reflected energy using as suitable transformation method such as Fourier transformation, Chirped-Z transformation to produce a time-domain record representing the reflection/scattering from said internal materials, and converting said amplitude and phase information from said sampled frequency spectrum of the reflected energy into time data, and calculating distance based on the known (or assumed) speed of light in each medium to produce data distance of said materials from a reference point and the thickness of selected materials in said process units;

wherein said frequencies of operation are selected within the range of 100 GHz to 3 THz but avoids specific frequencies where the gases exhibit strong absorption features;

said specific frequencies where the gases exhibit strong absorption features include the strongest such absorption features below 500 GHz at 183.5 GHz, 232.7 GHz, 293.8 GHz, 321.4 GHz, 325.3 GHz, 331.2 GHz, 336.5 GHz, 380.6 GHz, 390.6 GHz, 403.3 GHz, 426.1 GHz, 437.7 to 448.4 GHz, 463.4 GHz, 471.3 GHz, 475.1 GHz, and 488.6 GHz.

17. A terahertz/mm-wave system as defined in claim 16 wherein the specific frequency spectrum of the transmitted radiation is selected to lie within relatively transparent "windows" in the transmission spectrum of the gases inside said high temperature process units.

* * * * *